(12) United States Patent
Goutsis et al.

(10) Patent No.: US 8,425,623 B2
(45) Date of Patent: Apr. 23, 2013

(54) THICKENED OXIDATION PREPARATIONS

(75) Inventors: Konstantin Goutsis, Juechen (DE); Frank Janssen, Neuss (DE); Marc Krippahl, Moenchengladbach (DE)

(73) Assignee: Henkel AG & Co. KGAA (DE)

( * ) Notice: Subject to any disclaimer, the term of this patent is extended or adjusted under 35 U.S.C. 154(b) by 0 days.

(21) Appl. No.: 13/614,911

(22) Filed: Sep. 13, 2012

(65) Prior Publication Data

US 2013/0000662 A1 Jan. 3, 2013

Related U.S. Application Data

(63) Continuation of application No. PCT/EP2011/050802, filed on Jan. 21, 2011.

(30) Foreign Application Priority Data

Mar. 25, 2010 (DE) .......................... 10 2010 003 263

(51) Int. Cl.
*A61Q 5/10* (2006.01)
(52) U.S. Cl.
USPC ................ 8/405; 8/406; 8/408; 8/435; 8/552; 8/558
(58) Field of Classification Search .............. 8/405, 406, 8/408, 435, 552, 558
See application file for complete search history.

(56) References Cited

U.S. PATENT DOCUMENTS

2008/0083420 A1* 4/2008 Glenn et al. .................. 132/208
2009/0241272 A1 10/2009 Siracusa

FOREIGN PATENT DOCUMENTS

EP 1430874 A2 6/2004
WO 2005067874 A1 7/2005

OTHER PUBLICATIONS

European Patent Office, International Searching Authority, "International Search Report" mailed Feb. 6, 2013; International Appln. No. PCT/EP2011/050802, filed Jan. 21, 2011.

* cited by examiner

*Primary Examiner* — Eisa Elhilo
(74) *Attorney, Agent, or Firm* — Ingrassia Fisher & Lorenz, PC

(57) ABSTRACT

Thickened oxidative preparations are provided herein. In one embodiment, a cosmetic agent for changing the color of keratinic fibers is provided. The cosmetic agent includes a preparation (M1) containing a color-changing component and an oxidizing agent preparation (M2) containing in an aqueous, cosmetic carrier at least hydrogen peroxide as a chemical oxidizing agent and an anionic, polymeric thickener selected from crosslinked or uncrosslinked polyacrylic acid polymers. The cosmetic agent has a viscosity of about 5 to about 100 Pa s. The cosmetic agent is prepared directly before use by blending preparation (M1) with oxidizing agent preparation (M2).

13 Claims, No Drawings

THICKENED OXIDATION PREPARATIONS

CROSS-REFERENCE TO RELATED APPLICATION

This is a continuation of International Application No. PCT/EP2011/050802, filed Jan. 21, 2011, which was published under PCT Article 21(2) and which claims priority to German Application No. 10 2010 003 263.8, filed Mar. 25, 2010, which are all hereby incorporated in their entirety by reference.

TECHNICAL FIELD

The technical field is a cosmetic preparation for the oxidative color-changing of keratinic fibers, in particular human hair, which is mixed together from two components directly before use, wherein one of the components contains hydrogen peroxide and at least one uncrosslinked or crosslinked polyacrylic acid.

BACKGROUND

For the provision of color-changing cosmetic agents, especially for the skin or keratin-containing fibers such as for example human hair, the person skilled in the art is aware of diverse dyeing systems according to the requirements of the dyeing. The so-called oxidation dyes are used for long-lasting, intensive colorations with corresponding authentic characteristics. Dyes of this type usually comprise oxidation dye precursors, so-called developer components and coupler components which together under the influence of oxidizing agents or of atmospheric oxygen form the actual dyes. The oxidation dyes are distinguished by outstanding, long-lasting coloration results. In addition to dyeing, many consumers quite specifically wish to lighten or blond their own hair color. For this, the natural or synthetic dyes used to color the fibers are removed, mostly oxidatively, by employing appropriate oxidizing agents, such as for example hydrogen peroxide. For temporary colorations, usually colorants or toners are used that comprise so-called substantive dyes as the coloring component. These can likewise be incorporated along with oxidizing agents in lightening dyes.

In order to develop an optimal dyeing power, oxidative dyes generally need an alkaline pH for dyeing, especially between pH 9.0 and pH 11.5. For reasons of stability, oxidative dyes are usually only prepared directly prior to their application by blending a color-changing preparation and an oxidizing agent preparation. In order to stabilize oxidation dye precursors, the color-changing preparation usually has an alkaline pH, and in order to stabilize the oxidizing agent, the oxidizing agent preparation has an acidic pH, whereas the application mixture should have an alkaline pH in order to enable a good penetration of the dye precursor and the oxidizing agent into the keratinic fibers.

Moreover, the application period for attractive coloring results is usually between 10 and 60 minutes. The ready-for-use color-changing agent therefore needs to be formulated and packaged such that firstly, the colorant can be well dispersed onto the keratinic fibers being dyed and, secondly, however, that it remains in the fibers being dyed during the contact time. For this it is advantageous if the colorant has a certain viscosity that indeed enables the agent to be applied, but also allows the agent to remain at the place of application. This viscosity can be adjusted by polymeric thickeners in the ready-for-use colorant, wherein this thickener can be comprised in the color-changing preparation or in the oxidizing agent preparation.

In order to enable a good mixing of the color-changing preparation and oxidizing agent preparation, the color-changing preparation and oxidizing agent preparation advantageously exhibit good free flowability and the increased viscosity of the application mixture is then adjusted once the two components have been mixed. Established polymeric thickeners in cosmetic preparations are cellulose derivatives, such as hydroxyethyl cellulose or xanthan.

Accordingly, at least one object herein is to provide a color-changing agent, by means of which the above cited disadvantages of common color-changing agents are reduced. In particular, at least one object herein is to provide an oxidative color-changing agent for keratinic fibers which is characterized by a very good miscibility of both components: oxidizing agent preparation and color-changing preparation. The thus-resulting application mixture should possess an adequate viscosity, such that firstly the agent can be easily spread, secondly that it remains in place during the application without running out of the fibers.

SUMMARY

In accordance with an exemplary embodiment, a cosmetic agent for changing the color of keratinic fibers is provided. The cosmetic agent includes a preparation (M1) containing a color-changing component and an oxidizing agent preparation (M2) containing in an aqueous, cosmetic carrier at least hydrogen peroxide as a chemical oxidizing agent and an anionic, polymeric thickener selected from crosslinked or uncrosslinked polyacrylic acid polymers. The cosmetic agent has a viscosity of about 5 to about 100 Pa s. The cosmetic agent is prepared directly before use by blending preparation (M1) with oxidizing agent preparation (M2).

In accordance with another embodiment, a multi-component packaging unit includes a first container (C1) containing a color-changing preparation (M1) comprising a color-changing component in a cosmetic carrier and a second container (C2) containing an oxidizing agent preparation (M2) comprising in an aqueous, cosmetic carrier at least hydrogen peroxide as a chemical oxidizing agent and additionally an anionic, polymeric thickener selected from crosslinked or uncrosslinked polyacrylic acid polymers. The first container (C1) and the second container (C2) are packaged separately from one another.

In accordance with a further embodiment, a method for changing the color of keratinic fibers using a multi-component packaging unit containing a first container (C1) containing a color-changing preparation (M1) comprising a color-changing component in a cosmetic carrier and a second container (C2) containing an oxidizing agent preparation (M2) comprising in an aqueous, cosmetic carrier at least hydrogen peroxide as a chemical oxidizing agent and additionally an anionic, polymeric thickener selected from crosslinked or uncrosslinked polyacrylic acid polymers is provided. The first container (C1) and the second container (C2) are packaged separately from one another. The method includes combining the color-changing preparation (M1) with the oxidizing agent preparation (M2) in one of the first container (C1) or the second container (C2) to form a mixture, reclosing the container, shaking the mixture to form a resulting, ready-for-use color-changing agent, applying the resulting, ready-for-use color-changing agent onto the fibers, leaving the resulting, ready-for-use color-changing agent on the fibers for a contact period of about 5 to about 60 minutes, and rinsing the resulting, ready-for-use color-changing agent out of the fibers.

DETAILED DESCRIPTION

One method to achieve an adequate thickening uses polymeric thickeners, whose thickening properties change with the pH. This property can be particularly advantageously exploited if the polymeric thickener is comprised in the acidic oxidizing agent preparation, as this agent undergoes a large pH change on mixing to form the application preparation. Consequently, an anionic polymeric thickener is used that in alkaline pH conditions leads to a significant increase in viscosity. Homopolymers and copolymers of acrylic acid or methacrylic acid are particularly suitable anionic, polymeric thickeners.

However, it was surprisingly found that crosslinked or uncrosslinked polyacrylic acid polymers can be quite particularly advantageously incorporated in the oxidizing agent preparation for adjusting the viscosity. In the investigations the applicant unexpectedly found in this regard that in particular, the amount of the thickener to be added can be reduced without suffering any losses in the thickening. The oxidizing agent preparation therefore exhibits a good flowability that is enabled by thorough mixing with the color-changing preparation, for example by shaking. Finally, reducing the amount of thickener also offers advantages, in addition to raw material savings when manufacturing the agent, as due to the lower amounts of thickener, there is a reduced tendency for blockages in the pipes and valves in the production unit, and the unit can be more easily cleaned.

Accordingly, a first exemplary embodiment herein is a cosmetic agent for changing the color of keratinic fibers, which is prepared directly before the application by mixing a preparation (M1) containing in a cosmetic carrier at least one color-changing component and an oxidizing agent preparation (M2) containing in an aqueous, cosmetic carrier at least hydrogen peroxide as a chemical oxidizing agent and which has a viscosity of 5 to 100 Pa (pascals) s, preferably 10 to 30 Pa s, wherein the oxidizing agent preparation additionally contains at least one anionic, polymeric thickener, selected from crosslinked or uncrosslinked polyacrylic acid polymers.

Keratin-containing or keratinic fibers are herein understood to mean furs, wool, feathers and in particular human hair. Although the contemplated uses are primarily suitable for dyeing and/or lightening keratin-containing fibers, in principle nothing prevents their use in other fields.

The preparations contemplated herein comprise the active substances in a cosmetic carrier. In the context herein, this cosmetic carrier is aqueous, alcoholic or aqueous-alcoholic. As used herein, aqueous-alcoholic carriers are understood to mean water-containing solutions, containing about 3 to about 70% by weight of a C1-C4 alcohol, in particular, ethanol or isopropanol, based on the total weight of the application mixture. The agents contemplated herein can additionally comprise further organic solvents, such as for example 4-methoxybutanol, ethyl diglycol, 1,2-propylene glycol, n-propanol, n-butanol, n-butylene glycol, glycerin, diethylene glycol monoethyl ether, and diethylene glycol mono-n-butyl ether. Preference here is given to all water-soluble organic solvents. In the context herein, an aqueous carrier contains at least about 30 wt %, especially at least about 50 wt % water, based on the total weight of the preparation. For the purposes of dyeing the hair, such carriers are, for example, creams, emulsions, gels or also surfactant-containing foaming solutions, such as, for example, shampoos, foam aerosols or other preparations that are suitable for use on the hair. Emulsions and gels represent preferred carriers, wherein emulsions are particularly preferred.

The ready-for-use colorants inventively exhibit a sufficient viscosity that allows the agent firstly to be easily applied onto the fibers being colored and to be dispersed at the target area, but secondly for the agent to remain in the region being colored and not to run out. For this, the contemplated agents possess a viscosity of about 5 to about 100 Pa s, for example about 10 to about 30 Pa s, such as about 12 to about 25 Pa s. The contemplated listed viscosities each refer to viscosities that were measured with a rotational viscosimeter (Brookfield, 22° C., spindle #5, 4 rpm).

The cosmetic agent is prepared prior to the application by mixing a color-changing preparation (M1) with an oxidizing agent preparation (M2).

In this regard, in an embodiment, the color-changing preparation (M1) contains at least one color-changing component. As the color-changing component in agent (M1), lightening agents can be added as additional bleach boosters that boost the action of the oxidizing agent, as well as chromophoric components.

Accordingly, in one embodiment the agent (M1) contains an additional bleach booster. In the context herein, peroxy compounds can be employed as the additional bleach boosters, also compounds that under perhydrolysis conditions afford aliphatic peroxycarboxylic acids and/or substituted perbenzoic acid, carbonic acid derivatives, alkyl carbonates, alkyl carbamates, silyl carbonates and silyl carbamates.

In an embodiment, the bleach booster is chosen from ammonium peroxydisulfate, alkali metal peroxydisulfates, ammonium peroxymonosulfate, alkali metal hydrogen peroxymonosulfates, alkali metal peroxydiphosphates and alkaline earth metal peroxides. Particularly suitable bleach boosters are ammonium peroxydisulfate, potassium peroxydisulfate, sodium peroxydisulfate, potassium hydrogen peroxymonosulfate, potassium peroxydiphosphate, magnesium peroxide and barium peroxide. Further exemplary agents comprise at least one inorganic salt, selected from peroxymonosulfates and/or peroxydisulfates as the bleach booster. Moreover, the agents contemplated herein can comprise at least two different peroxydisulfates. In this regard, suitable peroxydisulfate salts are combinations of ammonium peroxydisulfate and potassium peroxydisulfate and/or sodium peroxydisulfate. The ready for use agent contains the peroxy compounds in an amount of, for example, about 0.1 to about 25 wt %, such as in an amount of about 0.5 to about 15 wt %, based on the total weight of the ready for use agent.

The persulfate salts or peroxydisulfate salts are generally anhydrous and added in the form of an optionally dedusted powder, paste or in the form of a compressed molded body. The anhydrous agents (M1) can comprise an additional bleach booster, instead of and/or in addition to the solid peroxy compounds.

Although in principle no limitations exist in regard to the formulation of the agent (M1), in an embodiment, the agent (M1) is formulated in an anhydrous manner if the agent (M1) contains an additional bleach booster as the color-changing component. In the context herein, anhydrous means a water content, based on the agent (M1), of less than about 5 wt %, especially less than about 2 wt %. Agents (M1) that comprise less than about 0.1 wt % water can be particularly suitable. The agent (M1) is preferably formulated as a powder or an anhydrous paste.

In another embodiment, the agent (M1) comprises at least one cationic pyridinium derivative as the bleach booster.

Exemplary compounds include, but are not limited to, 4-acylpyridinium derivatives and 2-acylpyridinium derivatives. In this regard, 2-acetyl-1-methylpyridinium p-toluenesulfonate and 4-acetyl-1-methylpyridinium p-toluenesulfonate are particularly suitable. Additionally preferred cationic pyridinium derivatives are cationic 3,4-dihydroisoquinolinium derivatives. N-methyl-3,4-dihydroisoquinolinium p-toluenesulfonate is particularly preferred.

The bleach boosters employed in addition to, or instead of, peroxy compounds are comprised in the cosmetic agents for example in amounts of about 0.05 to about 10% by weight, such as in amounts of about 0.2 to about 5% by weight, each based on the total weight of the ready-for-use agent.

In order to further increase the lightening power, an optionally hydrated SiO2 compound can be added as the bleach booster to the composition (M1). Although small amounts of the optionally hydrated SiO2 compounds already increase the lightening power, in an embodiment the optionally hydrated SiO2 compounds are used in amounts of about 0.05% by weight to about 15% by weight, for example in amounts of about 0.15% by weight to about 10% by weight, such as in amounts of about 0.2% by weight to about 5% by weight, in each case based on the anhydrous composition contemplated herein. In this regard, the quantities each reflect the content of the SiO2 compounds (without their water content) in the agents. Preferred optionally hydrated SiO2 compounds are silicic acids, their oligomers and polymers, and their salts. The optionally hydrated SiO2 compounds can be present in various forms. As contemplated herein, the SiO2 compounds are used in the form of silica gels or as a water-glass, such as water-glasses that are formed from a silicate of the formula (SiO2)n(Na2O)m(K2O)p, where n is a positive rational number and m and p, independently of one another, are a positive rational number or are 0, with the provisos that at least one of the parameters m or p is different from 0 and the ratio between n and the sum of m and p is between 1:4 and 4:1. Metasilicates can be employed, in particular those in the above Formula which are characterized by the ratio between n and the sum of m and p being less than or equal to 1, and which can be considered as chain-like polymeric structures of the anion [SiO3]2-. In this regard, sodium metasilicate of the Formula [NaSiO3]x, can be used.

In another embodiment, the agent (M1) contains chromophoric components as the color-changing component. Consequently, the contemplated agents can additionally comprise at least one chromophoric component that is preferably selected from at least one oxidation dye precursor and/or from at least one substantive dye.

Therefore, in an embodiment, agents for changing the color of keratinic fibers comprise at least one oxidation dye precursor. The lighteners comprise at least one oxidation dye precursor of the developer type (developer component) as the oxidation dye precursor, for example in combination with at least one oxidation dye precursor of the coupler type.

Exemplary oxidation dye precursors of the developer type are p-phenylenediamine derivatives. Suitable p-phenylenediamines are chosen from one or more compounds of the group that consists of p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(2-hydroxyethyl)-p-phenylenediamine, 4-N,N-bis-(2-hydroxyethyl)-amino-2-methylaniline, 4-N,N-bis-(2-hydroxyethyl)-amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane as well as their physiologically acceptable salts. Inventively particularly preferred p-phenylenediamine derivatives are selected from at least one compound of the group p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine as well as the physiologically acceptable salts of these compounds.

In another embodiment, compounds that comprise at least two aromatic nuclei that are substituted by amino and/or hydroxyl groups are used as the developer component. Exemplary binuclear developer components are selected from at least one of the following compounds: N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenyl)-ethylendiamine, N,N'-bis-(4'-aminophenyl)tetramethylenediamine, N,N'-bis-(2-hydroxyethyl)-N,N'-bis-(4'-aminophenyl)-tetramethylenediamine, N,N'-bis-(4-(methylamino)phenyl)tetramethylenediamine, N,N'-diethyl-N,N'-bis-(4'-amino-3'-methylphenyl)ethylenediamine, bis-(2-hydroxy-5-aminophenyl)-methane, N,N'-bis-(4'-aminophenyl)-1,4-diazacycloheptane, N,N'-bis-(2-hydroxy-5-aminobenzyl)-piperazine, N-(4'-aminophenyl)-p-phenylendiamine and 1,10-bis-(2',5'-diaminophenyl)-1,4,7,10-tetraoxadecane as well as their physiologically acceptable salts. Other suitable binuclear developer components are selected from among N,N'-bis-(2-hydroxyethyl)-N,N'-bis-(4-aminophenyl)-1,3-diamino-2-propanol, bis-(2-hydroxy-5-aminophenyl)methane, 1,3-bis-(2,5-diaminophenoxy)-2-propanol, N,N'-bis(4-aminophenyl)-1,4-diazacycloheptane, 1,10-bis-(2,5-diaminophenyl)-1,4,7,10-tetraoxadecane or one of their physiologically acceptable salts.

In addition, a p-aminophenol derivative or one of its physiologically acceptable salts may be used as the developer component. Exemplary p-aminophenols are p-aminophenol, N-methyl-p-aminophenol, 4-amino-3-methyl-phenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol as well as their physiologically acceptable salts. p-Aminophenol, 4-amino-3-methylphenol, 4-amino-2-aminomethylphenol, 4-amino-2-(1,2-dihydroxyethyl)phenol and 4-amino-2-(diethylaminomethyl)phenol are particularly suitable compounds.

Furthermore, the developer component can be selected from o-aminophenol and its derivatives, such as, for example 2-amino-4-methylphenol, 2-amino-5-methylphenol or 2-amino-4-chlorophenol.

In addition, the developer component can be chosen from heterocyclic developer components, such as, for example, from pyrimidine derivatives, pyrazole derivatives, pyrazolopyrimidine derivatives and pyrazolopyrazole derivatives and their physiologically acceptable salts. Exemplary pyrimidine derivatives include, but are not limited to, the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Preferred pyrazole derivatives are the compounds that are selected from 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl) amino-1,3-dimethylpyrazole, as well as their physiologically acceptable salts, especially however 4,5-diamino-1-(2-hydroxyethyl)pyrazole. Other suitable pyrazolopyrimidines are the compounds selected from among pyrazolo[1,5-a]pyrimidine-3,7-diamine, 2,5-dimethyl-pyrazolo[1,5-a]pyrimidine-3,7-diamine, pyrazolo[1,5-a]pyrimidine-3,5-diamine, 2,7-dimethyl-pyrazolo[1,5-a]pyrimidine-3,5-diamine, 3-aminopyrazolo[1,5-a]pyrimidin-7-ol, 3-amino-pyrazolo[1,5-a]pyrimidin-5-ol, 2-(3-aminopyrazolo[1,5-a]pyrimidin-7-ylamino)ethanol, 2-(7-amino-pyrazolo[1,5-a]pyrimidin-3-ylamino)ethanol, 2-[(3-aminopyrazolo[1,5-a]pyrimidin-7-yl)-(2-hydroxy-ethyl)-amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine as well as their physiologically acceptable salts and their tautomeric forms, if a tautomeric equilibrium is present. 2,3-Diamino-6,7-dihydro-1H,5H-pyrazolo[1,2-a]pyrazol-1-one is preferred.

Further exemplary developer components are selected from at least one compound from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-2-propanol, bis-(2-hydroxy-5-aminophenyl)methane, 1,3-bis-(2,5-diaminophenoxy)-2-propanol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxy-ethyl)phenol and 4-amino-2-(diethylaminomethyl)phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one as well as the physiologically acceptable salts of these compounds. Quite particularly preferred developer components are p-toluylenediamine, 2-(2-hydroxyethyl)-p-phenylenediamine, 2-methoxy-methyl-p-phenylenediamine, N-(4-amino-3-methylphenyl)-N-[3-(1H-imidazol-1-yl)propyl]amine, and/or 4,5-diamino-1-(2-hydroxyethyl)pyrazole as well as the physiologically acceptable salts of these compounds.

The developer components are, for example, used in an amount of about 0.0001 to about 0.5 wt %, such as about 0.001 to about 0.2 wt %, in each case based on the ready-for-use agent.

Coupler components alone, in the context of the oxidative dyeing, do not form any significant coloration; rather they need the presence of developer components. Therefore, in an embodiment, when using at least one coupler component, at least one developer component is also used. In the context herein, coupler components allow at least one substitution of a chemical group of the coupler by the oxidized form of the developer component. A covalent bond is formed between coupler component and developer component.

Exemplary coupler components are selected as at least one compound from one of the following classes: m-aminophenol, o-aminophenol, m-diaminobenzene, o-diaminobenzene and/or their derivatives; naphthalene derivatives with at least one hydroxyl group; di or trihydroxybenzene; pyridine derivatives; pyrimidine derivatives; certain indole derivatives and indoline derivatives; pyrazolone derivatives (for example 1-phenyl-3-methylpyrazol-5-one); morpholine derivatives (for example 6-hydroxybenzomorpholine or 6-aminobenzomorpholine); quinoxaline derivatives (for example 6-methyl-1,2,3,4-tetrahydroquinoxaline) as well as mixtures of two or more compounds from one or more of these classes.

Exemplary m-aminophenol coupler components are chosen from at least one compound from the group consisting of 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-diethylaminophenol, N-cyclopentyl-3-aminophenol, 1,3-dihydroxy-5-(methylamino)benzene, 3-ethyl-amino-4-methylphenol, 2,4-dichloro-3-aminophenol and their physiologically acceptable salts.

Exemplary m-diaminophenol coupler components are chosen from at least one compound from the group consisting of m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)-amino]-4,5-dimethylphenyl}amino) ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene and their physiologically acceptable salts.

Exemplary o-diaminobenzene coupler components are selected from at least one compound from the group consisting of 3,4-diaminobenzoic acid and 2,3-diamino-1-methylbenzene and their physiologically acceptable salts.

Exemplary naphthalene derivatives with at least one hydroxyl group are selected from at least one compound from the group consisting of 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Exemplary di or trihydroxybenzenes and their derivatives are selected from at least one compound from the group consisting of resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Exemplary pyridine derivatives are selected from at least one compound from the group consisting of 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and their physiologically acceptable salts.

Exemplary pyrimidine derivatives are selected from at least one compound from the group consisting of 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and their physiologically acceptable salts.

Exemplary indole derivatives are selected from at least one compound from the group consisting of 4-hydroxyindole, 6-hydroxyindole and 7-hydroxyindole and their physiologically acceptable salts.

Exemplary indoline derivatives are selected from at least one compound from the group consisting of 4-hydroxyindoline, 6-hydroxyindoline and 7-hydroxyindoline and their physiologically acceptable salts.

As contemplated herein, exemplary coupler components are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)-ethanol, 1,3-bis(2,4-diaminophenoxy) propane, 1-methoxy-2-amino-4-(2-hydroxyethylamino)-benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or their physiologically acceptable salts.

Resorcinol, 2-methylresorcinol, 5-amino-2-methylphenol, 3-aminophenol, 2-(2,4-diaminophenoxy)ethanol, 1,3-bis(2, 4-diaminophenoxy)propane, 1-methoxy-2-amino-4-(2'-hydroxyethylamino)benzene, 2-amino-3-hydroxypyridine and 1-naphthol as well as their physiologically acceptable salts are quite particularly preferred.

The coupler components are, for example, used in an amount of about 0.0001 to about 0.5 wt %, such as about 0.001 to about 0.2 wt %, in each case based on the ready-for-use agent.

Here, developer components and coupler components are generally used in approximately equimolar amounts relative to one another. Although the equimolar use has also proven to be expedient, a certain excess of individual oxidation dye precursors is not disadvantageous, meaning that developer components and coupler components may be present in a molar ratio of about 1 to about 0.5 to about 1 to about 3, in particular, about 1 to about 1 to about 1 to about 2.

The agents (M1) contemplated herein can further comprise a substantive dye. These are dyes that are directly absorbed onto the hair and do not require any oxidative process to develop the color. Substantive dyes can be sub-divided into anionic, cationic and non-ionic substantive dyes. Substantive dyes are usually nitrophenylenediamines, nitroaminophenols, azo dyes, anthraquinones or indophenols. The substantive dyes, for example, are employed in quantities of about 0.0001 to about 5.0 wt %, such as about 0.001 to about 1.5 wt %, each based on the total end-use preparation. The total amount of substantive dyes is, for example, maximum about 1.0 wt %.

Exemplary anionic substantive dyestuffs are known compounds with the international designations or trade names Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52, Bromophenol blue and Tetrabromophenol blue. Exemplary cationic substantive dyes are cationic triphenylmethane dyes, such as Basic Blue 7, Basic Blue 26, Basic Violet 2 and Basic Violet 14, aromatic systems that are substituted with a quaternary nitrogen group, such as for example Basic Yellow 57, Basic Red 76, Basic Blue 99, Basic Brown 16 and Basic Brown 17, as well as substantive dyes that comprise a heterocycle that exhibits at least one quaternary nitrogen atom, in particular Basic Yellow 87, Basic Orange 31 and Basic Red 51. The cationic substantive dyes that are commercialized under the trade name Arianor® are likewise quite particularly suitable cationic substantive dyes for use herein. Non-ionic nitro and quinone dyes and neutral azo dyes are particularly suitable as non-ionic substantive dyes. Exemplary non-ionic substantive dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl) amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol. Exemplary dye combinations are those with at least the combination of Tetrabromophenol Blue and Acid Red 92; Tetrabromophenol Blue and Acid Red 98; Tetrabromophenol Blue and Acid Red 94; Tetrabromophenol Blue and Acid Red 87 or Tetrabromophenol Blue and Acid Red 51.

In an embodiment, the preparation (M1) further contains an alkalizer for adjusting a basic pH of the application mixture and in particular for stabilizing dye precursors. The alkalizers that can be used for adjusting the pH are typically selected from inorganic salts, especially from the alkali metals and alkaline earth metals, organic alkalizers, especially amines, basic amino acids and alkanolamines, and ammonia.

Exemplary useable organic alkalizers are selected from alkanolamines from primary, secondary or tertiary amines containing a C2-C6 alkyl parent substance that carries at least one hydroxyl group. Suitable alkanolamines are selected from the group 2-aminoethan-1-ol (monoethanolamine), 2-amino-2-methylpropan-1-ol and 2-amino-2-methyl-propane-1,3-diol. A preferred alkanolamine is monoethanolamine. Suitable basic amino acids are lysine, arginine and ornithine. The inorganic alkalizers can be selected from the group consisting of sodium hydroxide, potassium hydroxide, calcium hydroxide, barium hydroxide, sodium phosphate, potassium phosphate, sodium silicate, potassium silicate, ammonium hydrogen carbonate, sodium hydrogen carbonate, potassium hydrogen carbonate, ammonium carbonate, sodium carbonate and potassium carbonate.

According to another embodiment contemplated herein, the preparation (M1) additionally contains at least one alkalizer selected from ammonia, sodium hydroxide, sodium carbonate, potassium hydroxide, potassium carbonate, sodium hydrogen carbonate, ammonium carbonate, ammonium hydrogen carbonate, arginine, histidine, monoethanolamine and/or 2-amino-2-methylpropanol.

The oxidizing agent preparation (M2) contains in an aqueous, cosmetic carrier at least hydrogen peroxide as the chemical oxidizing agent, in another embodiment. In this regard, hydrogen peroxide is either added as an aqueous solution or in the form of a solid addition compound of hydrogen peroxide onto inorganic or organic compounds, such as, for example, sodium perborate, sodium percarbonate, magnesium percarbonate, sodium percarbamide, polyvinyl pyrrolidone nH2O2 (n is a positive integer greater than 0), urea peroxide and melamine peroxide. Exemplary aqueous phases (I) comprise aqueous hydrogen peroxide solutions. The concentration of a hydrogen peroxide solution is determined firstly by the legal requirements and secondly by the desired effect. Hydrogen peroxide solutions of about 3 wt % to about 12 wt % concentration in water are suitably used as the aqueous phase.

Here, exemplary ready-for-use agents for changing the color of keratinic fibers comprise about 0.5 to about 15 wt %, for example about 1 to about 12 wt %, for example about 1.5 to about 9 wt %, such as about 2 to about 8 wt % hydrogen peroxide (calculated as 100% concentrated H2O2), each calculated on the total weight of the agent.

In a further embodiment, the oxidizing preparation (M2) further contains an anionic, polymeric thickener that is selected from crosslinked or uncrosslinked polyacrylic acid polymers. Exemplary polyacrylic acid polymers concern polymers of acrylic acid itself or C1-C4 alkyl acrylates, wherein in the latter case the polymer was subjected to a subsequent basic saponification of the ester.

Crosslinked polyacrylic acid polymers are understood to include those polymers, to which a certain amount of bi or polyfunctional monomers for the crosslinking was added during the polymerization. Here, preferred crosslinking agents are ethylene glycol dimethacrylate, 1,9-decadiene, divinylbenzene as well as allyl ethers of pentaerythritol, of sucrose, of ethylene glycol and of propylene glycol. Suitable polymeric compounds are commercially available for example under the trade name Carbopol® and under the INCI name Carbomer.

An exemplary anionic, polymeric thickener has a certain average molecular weight, in order firstly to achieve an adequate thickening of the application mixture and secondly to ensure a sufficient solubility in the aqueous phase (I). Suitable thickeners have an average molecular weight of at least about 200,000 g/mol, for example at least 350,000 g/mol, such as at least about 500,000 g/mol.

A particularly preferred anionic, polymeric thickener is sold under the trade name Carbomer 954 from the Lubrizol company (Noveon).

In an embodiment, the oxidizing agent preparation (M2) contains the anionic, polymeric thickener(s) in amounts of about 0.01 to about 20 wt %, for example about 0.1 to about 5 wt %, each relative to the total weight of the preparation (M2).

In another embodiment, the oxidizing agent preparation (M2) possesses a weakly acid pH, for example a pH of about pH 2 to about pH 6, such as about pH 2.5 to about pH 4.5. In the context herein, the pH values refer to those measured at a temperature of 22° C. The person skilled in cosmetics commonly uses established acidifiers and alkalizers to adjust the pH. Exemplary acidifiers are food acids, such as for example lactic acid, citric acid, acetic acid, malic acid or tartaric acid, as well as diluted mineral acids.

The preparation (M2) in addition may comprise only a minor fraction of surface active, for example anionic surface active, substances. Accordingly, in one embodiment herein, the preparation (M2) additionally contains at least one anionic surfactant in a weight fraction of about 0.05 to about 1.5 wt %, relative to the total weight of the preparation (M2).

In the context herein, emulsifiers and surfactants are considered as the surface active substances. Surface active substances are characterized by hydrophobic and hydrophilic structural features and thereby enable the phases when mixed together to form micelles and stable emulsions. As used herein, anionic surfactants are all anionic surface-active materials that are suitable for use on the human body. They are characterized by a water-solubilizing anionic group, such as for example a carboxylate, sulfate, sulfonate or phosphate group and a lipophilic alkyl group containing about 8 to 30 carbon atoms. In addition, the molecule may comprise glycol or polyglycol ether groups, ester, ether and amide groups as well as hydroxyl groups. Examples of such anionic surfactants are, each in the form of the sodium, potassium and ammonium salts as well as in the form of the mono, di and trialkanol-ammonium salts with 2 to 4 carbon atoms in the alkanol group, linear and branched fatty acid with 8 to 30 carbon atoms (soaps); ether carboxylic acids, in particular of the formula RO(CH2CH2O)xCH2COOH, in which R is a linear alkyl group with 8 to 30 carbon atoms and x=0 or 1 to 16; acyl sarcosides; acyl taurides; acyl isethionates; succinic acid mono and diesters as well as succinic acid monoalkyl polyoxyethyl esters; linear alkane sulfonates; linear α-olefin sulfonates; sulfonates of unsaturated fatty acids; α-sulfofatty acid methyl esters of fatty acids; alkyl sulfates and alkyl ether sulfates, in particular of the Formula RO(CH2CH2O)xSO3H, in which R stands for a linear alkyl group with 8 to 30 carbon atoms and x for 0 or a number from 1 to 12; mixtures of surface active hydroxyl sulfonates, sulfated hydroxyalkyl polyethylene glycol ethers and/or hydroxyalkylene propylene glycol ethers; esters of tartaric acid and citric acid with alcohols; alkyl and/or alkenyl ether phosphates of the Formula RO(C2H4O)xP(=O)(OH)(OR'), in which R stands for an aliphatic, optionally unsaturated hydrocarbon group with 8 to 30 carbon atoms, R' for hydrogen, a group (CH2CH2O)yR and x and y independently of one another stands for a number from 1 to 10; sulfated fatty acid alkylene glycol esters of the Formula RC(O)O(alkO)nSO3H, in which R stands for a linear or branched, aliphatic, saturated and/or unsaturated alkyl group with 6 to 22 carbon atoms, alk for CH2CH2, CHCH3CH2 and/or CH2CHCH3 and n for a number from 0.5 to 5; as well as monoglyceride sulfates and monoglyceride ether sulfates.

As contemplated herein, the oxidizing agent preparation can be applied to the hair together with a catalyst that further activates the oxidation of the dye precursors. Such catalysts are for example certain enzymes, iodides, quinones or metal ions. Suitable enzymes are, for example, peroxidases, which can considerably enhance the effect of small amounts of hydrogen peroxide. An addition of certain metal ions or metal complexes can likewise be preferred. Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$, $Ce^{4+}$, $V^{3+}$, $Co^{2+}$, $Ru^{3+}$ and $Al^{3+}$. $Zn^{2+}$, $Cu^{2+}$ and $Mn^{2+}$ are particularly suitable here.

In addition it has proven advantageous when the oxidizing agent preparations comprise at least one stabilizer or complexant. Exemplary stabilizers include phenacetin, alkali metal benzoates (sodium benzoate) and salicylic acid.

The addition of so-called complexants is also contemplated herein. Complexants are substances that can complex metal ions. Preferred complexants are so-called chelating agents, i.e. substances that form cyclic compounds with metal ions, wherein a single ligand occupies more than one coordination site on a central atom, i.e. is at least bidentate. Suitable and—in the context herein—preferred chelating agents are, for example polyoxycarboxylic acids, polyamines, ethylenediaminetetraacetic acid (EDTA) and nitrilotriacetic acid (NTA) and hydroxyethane diphosphonic acids and their alkali metal salts. Complexing polymers, i.e. polymers which, either in the main chain itself or laterally thereof, carry functional groups which are capable of acting as ligands and which react with suitable metal atoms, generally to form chelate complexes, may also be used. In this regard, the polymer-bound ligands of the resulting metal complexes can originate from one macromolecule or even from various polymer chains. Exemplary complexants are nitrogen-containing polycarboxylic acids, especially EDTA, and phosphonates, preferably hydroxyalkane or aminoalkane phosphonates and especially 1,1-hydroxyethane-1,1-diphosphonate (HEDP) or its di- or tetrasodium salt and/or ethylenediaminetetramethylene phosphonate (EDTMP) or its hexasodium salt and/or diethylenetriaminepentamethylene phosphonate (DTPMP) or its hepta or octasodium salt.

Exemplary ready-for-use agents include aqueous, free-flowing preparations. The agents can furthermore comprise all active substances, additives and auxiliaries known for such preparations. The ready-for-use agents as a mixture of agents (M1) and (M2) can here comprise surface active substances, selected from the above listed anionic, as well as non-ionic, zwitterionic, amphoteric and cationic surfactants.

Zwitterionic surfactants are designated as those surface-active compounds that carry at least one quaternary ammonium group and at least one carboxylate, sulfonate or sulfate group in the molecule. Exemplary suitable zwitterionic surfactants are the so-called betaines such as the N-alkyl-N,N-dimethylammonium glycinates, for example the cocoalkyl dimethylammonium glycinate, N-acylaminopropyl-N,N-dimethylammonium glycinates, for example the cocoacylaminopropyl-dimethylammonium glycinate, and 2-alkyl-3-carboxymethyl-3-hydroxyethyl imidazolines with 8 to 18 carbon atoms in each of the alkyl or acyl groups, as well as cocoacylaminoethyl hydroxyethylcarboxymethyl glycinate.

A preferred zwitterionic surfactant is the fatty acid amide derivative, known under the INCI name Cocamidopropyl Betaine.

Ampholytic surfactants are understood to include such surface-active compounds that, apart from a C8-C24 alkyl or acyl group, comprise at least one free amino group and at least one —COOH or —SO3H group in the molecule, and are able to form internal salts. Usual ampholytic surfactants are N-alkylglycines, N-alkylamino propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids, each with about 8 to 24 carbon atoms in the alkyl group. Particularly preferred amphoteric surfactants are N-cocoalkylamino propionate, cocoacylaminoethylamino propionate and C12-C18 acyl sarcosine.

Non-ionic surfactants and emulsifiers comprise e.g. a polyol group, a polyalkylene glycol ether group or a combination of polyol and polyglycol ether groups as the hydrophilic group. Such compounds are for example addition products of 1 to 50 moles ethylene oxide and/or 0 to 5 moles propylene oxide to linear and branched fatty alcohols containing 8 to 30 carbon atoms, to fatty acids containing 8 to 30 carbon atoms and to alkyl phenols containing 8 to 15 carbon atoms in the alkyl group; methyl or C2-C6 alkyl group end blocked addition products of 1 to 50 moles ethylene oxide and/or 1 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, such as, for example, the commercially available types Dehydol® LS, Dehydol® LT (Cognis); polyglycerin esters and alkoxylated polyglycerin esters, such as for example poly(3)glycerin diisostearate (commercial product: Lameform TGI (Henkel)) and poly(2)glycerin polyhydroxystearate (commercial product: Dehymuls PGPH (Henkel)); polyol fatty acid esters, such as for example the commercial product Hydagen HSP (Cognis) or Sovermol types (Cognis); higher alkoxylated, propoxylated and in particular ethoxylated, mono, di and triglycerides with alkoxylation degrees greater than 5, such as for example glycerin monolaurate+20 ethylene oxide and glycerin monostearate+20 ethylene oxide; amine oxides; hydroxy mixed ethers; sorbitol esters of fatty acids and addition products of ethylene oxide to sorbitol esters of fatty acids such as for example the polysorbates and sorbitol monolaurate+20 moles ethylene oxide (EO); sugar esters of fatty acids and addition products of ethylene oxide on sugar esters of fatty acids; addition products of ethylene oxide on fatty acid alkanolamides and fatty amines; fatty acid-N-alkyl glucamides; alkyl phenols and alkylphenol alkoxylates with 6 to 21, in particular 6 to 15 carbon atoms in the alkyl chain and 5 to 30 ethylene oxide and/or propylene oxide units; alkyl polyglycosides corresponding to the general Formula RO—(Z)x, wherein R stands for alkyl, Z for sugar and x for the number of sugar units.

As contemplated herein, the non-ionic emulsifiers can further include the polymerization products of ethylene oxide and propylene oxide on saturated or unsaturated fatty alcohols; fatty acid esters of polyhydric alcohols with saturated or unsaturated fatty acids; alkyl esters of saturated or unsaturated fatty acids or alkylphenols and their alkoxylates; in particular ethylene glycol ethers of fatty alcohols; mixed ethylene and propylene glycol ethers with fatty alcohols; fatty acid esters on sorbitol or polyethylene glycol; esters of non-hydroxylated C6-C30 alkyl monocarboxylic acids with polyethylene glycol; and addition products of alkylphenols on ethylene and/or propylene oxide.

Cationic surfactants of the type quaternary ammonium compounds, the ester quats and the amido amines are suitable in ready-for-use agents. Exemplary quaternary ammonium compounds are ammonium halides, especially chlorides and bromides, such as alkyltrimethylammonium chlorides, dialkyldimethylammonium chlorides and trialkylmethylammonium chlorides, as well as the imidazolium compounds known under the INCI names Quaternium-27 and Quaternium-83. The quaternized protein hydrolyzates illustrate further usable cationic surfactants. Alkylamido amines are normally manufactured by the amidation of natural or synthetic fatty acids and fatty acid fractions with dialkylamino amines, such as stearamidopropyldimethylamine) Likewise preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are marketed, for example, under the trade names Stepantex®, Dehyquart® and Armocare®. The products Armocare® VGH-70, an N,N-bis(2-palmitoyloxyethyl)dimethylammonium chloride, as well as Dehyquart® F-75, Dehyquart® C-4046, Dehyquart® L80 and Dehyquart® AU 35 are examples of such esterquats. The agents used herein comprise the cationic surfactants in quantities of about 0.05 to about 10 wt %, based on the total agent. Quantities of about 0.1 to about 5 wt % are particularly suitable.

In an exemplary embodiment, non-ionic, zwitterionic and/or amphoteric surfactants as well as mixtures thereof can be preferred.

Furthermore, the agents contemplated herein can comprise additional active substances, auxiliaries and additives, such as for example non-ionic polymers (such as for example vinyl pyrrolidinone/vinyl acrylate copolymers, polyvinyl pyrrolidinone, vinyl pyrrolidinone/vinyl acetate copolymers, polyethylene glycols and polysiloxanes); zwitterionic and amphoteric polymers (acrylamidopropyl-trimethylammonium chloride/acrylate copolymers and octylacrylamide/methyl methacrylate/tert-butylaminoethyl methacrylate/2-hydroxypropyl methacrylate copolymers); thickeners like agar-agar, guar gum, alginates, xanthane gum, gum arabica, karaya gum, locust bean flour, linseed gums, dextrans, cellulose derivatives, e.g. methyl cellulose, hydroxyalkyl cellulose and carboxymethyl cellulose, starch fractions and derivatives like amylose, amylopectin and dextrins, clays such as e.g. bentonite or synthetic hydrocolloids such as e.g. polyvinyl alcohol; structurants (such as sugar, maleic acid and lactic acid) and texturizers (such as sugar esters, polyol esters or polyalkyl ethers); protein hydrolyzates of vegetal or animal origin (elastin-, collagen-, keratin-, milk albumin-, soya protein- and wheat protein-hydrolyzates, their condensation products with fatty acids); perfume oils, care oils; cyclodextrins; defoamers such as silicones; dyes for dyeing the agent; anti-dandruff active substances (Piroctone Olamine, Zinc Omadine and Climbazol); light protective agents (in particular derivatized benzophenones, cinnamic acid derivatives and triazine); active substances (such as allantoin, pyrrolidinone carboxylic acids, cholesterol and their salts); waxes (such as fatty alcohols, beeswax, montan wax and paraffins); swelling and penetrants (such as glycerin, propylene glycol monoethyl ether, carbonates, hydrogen carbonates, guanidines, ureas as well as primary, secondary and tertiary phosphates); opacifiers (such as latex, styrene/PVP copolymers and styrene/acrylamide copolymers); pearlizers (such as ethylene glycol mono and distearate as well as PEG-3-distearate); propellants such as propane-butane mixtures, N2O, dimethyl ether, CO2 and air; antioxidants.

The person skilled in the art will select these additional materials as a function of the desired properties of the agent. With regard to further optional ingredients and their amounts used, reference is expressly made to the relevant handbooks known to the person skilled in the art, for example the monograph by K. Schrader, Grundlagen and Rezepturen der Kosmetika, 2nd edition, Hüthig Buch Verlag, Heidelberg, 1989.

In an embodiment, the ready-for-use agents of the oxidizing agent preparation (M2) and color-changing agent (M1) have a pH in the range of about 6 to about 12. Exemplary agents exhibit an alkaline pH. Another embodiment contemplated herein consists in that the ready for use agent exhibits a pH between about 8.5 and about 11.5, for example between about 9.5 and about 11.5. In the context herein, the pH values refer to those measured at a temperature of 22° C. Common acidifiers and alkalizers for adjusting the pH are listed further above.

The exemplary agent is prepared prior to use by mixing the color-changing preparation (M1) and the oxidizing preparation (M2). Accordingly, in an embodiment, the consumer is offered both preparations in a kit. Therefore, an exemplary presentation form of the ready-for-use agent is a separated packaging unit, in which each of the agents (M1) and (M2) are separately packaged.

Accordingly, a further embodiment herein is a multi-component packaging unit that contains at least two separate containers, wherein a first container (C1) contains a cosmetic agent (M1), containing in a cosmetic carrier at least one color-changing component, and a second container (C2), containing an oxidizing agent preparation (M2), containing in an aqueous, cosmetic carrier at least hydrogen peroxide as the chemical oxidizing agent and additionally an anionic, polymeric thickener, selected from crosslinked or uncrosslinked polyacrylic acid polymers.

In the context herein, a container is understood to mean an encasement that exists in the form of an optionally reusable bottle, a tube, a can, a small bag, a sachet or similar encasement. No limits are set for the encasement material. In an embodiment, however, encasements in this regard are made of glass or plastic.

In another embodiment, the agent (M1) of container (C1) represents the colorant preparation and contains an oxidation dye precursor and/or a substantive dye and/or a lightener.

Another embodiment is therefore a multi-component packaging unit wherein the color-changing preparation (M1) contains an oxidation dye precursor as the color-changing component.

Moreover, in an embodiment, the kit-of-parts contains an additional hair treatment agent, especially a conditioner, in a separate container. Furthermore, the packaging unit can include application aids, such as combs, brushes or small brushes, personal protective clothing, especially disposable gloves, as well as an optional instruction manual.

Another embodiment contemplated herein is a method for changing the color of keratinic fibers, in particular human hair, wherein both the agents (M1) and the (M2) from a multi-component packaging unit as described above are combined in one of the containers (C2) or (C1), the reclosed container is thereupon shaken, and the resulting ready-for-use color changing agent in this container is then applied onto the fibers, left on the fibers for a contact period of 5 to 60 minutes, and then rinsed out.

In the case of a chromophoric agent, an exemplary contact time is about 5 to about 40 minutes, for example about 10 to about 30 minutes. In the case of lightening or bleaching color-changing agents, an exemplary contact time is about 30 to about 60 minutes, for example about 40 to about 60 minutes. The application temperatures can be in a range of from about 15 to about 40° C. At the end of the contact time the remaining agent is removed by rinsing it out of the hair. There is no need to subsequently wash the hair with a shampoo if a strong surfactant-containing carrier was used.

For an improved mixing, in an embodiment the container (C2) that contains the oxidizing agent preparation (M2) possesses a re-closable opening, such as for example a snap-on or screw closure. This enables the simplified addition of the color-changing agent from container (C1) that itself is for example in the form of a small bag or sachet in the case of anhydrous, in particular powdery color-changing agents, or in the form of a tube in the case of free flowable color-changing agents. The individual preparations are mixed and within a short period of time the ready-for-use agent is applied onto the keratinic fibers.

A further embodiment herein is therefore a method for changing the color of keratinic fibers, in particular human hair, wherein the contents of the container (C1) from a multi-component packaging unit as described above are added to the container (C2), the reclosed container (C2) is thereupon shaken, and the resulting ready-for-use color changing agent in the container (C2) is then applied onto the fibers, left on the fibers for a contact period of about 5 to about 60 minutes, and then rinsed out.

Finally, an embodiment herein is wherein the resulting, ready-for-use color-changing agent has a viscosity of about 5 to about 100 Pa s, for example about 10 to about 30 Pa s, such as about 12 to about 25 Pa s (Brookfield, 22° C., spindle #5, 4 rpm).

The following examples are intended to illustrate the various embodiments herein in more detail, without limiting them in any way.

EXAMPLES

1) Coloring Cream FC

Table 1; Quantities in wt %

| | |
|---|---|
| Lanette D | 6.60 |
| Lorol C12-18 tech. | 2.40 |
| Eumulgin B 2 | 0.60 |
| Eumulgin B 1 | 0.60 |
| Akypo Soft 45HP | 10.00 |
| Protelan MST 35 | 6.00 |
| Texapon K 14 S Special, 70% | 2.80 |
| Product W 37194 | 3.75 |
| Sodium sulfite, anhydrous | 0.00 |
| Ascorbic acid | 0.10 |
| HEDP, aq., 60% | 0.20 |
| Sodium silicate 40/42 | 0.50 |
| Sodium hydroxide, aq., 50% | 1.00 |
| Glycine | 1.00 |
| Taurine | 1.00 |
| alpha-Liponic acid | 0.20 |
| Litchiderm LS 9704 | 1.00 |
| p-Toluylenediamine sulfate | 2.81 |
| 2,4-Diaminophenoxyethanol 2HCl | 0.44 |
| Resorcinol | 1.00 |
| m-Aminophenol | 0.20 |
| Monoethanolamine | 9.20 |
| Perfume | qs |
| Water, deionized | ad 100 |

Raw materials: Lanette D (INCI name: Cetearyl alcohol; Cognis); Lorol C12-18 techn. (INCI name: Coconut alcohol; Cognis); Eumulgin B2 (INCI name: Ceteareth-20; Cognis); Eumulgin B1 (INCI name: Ceteareth-12; Cognis); Akypo Soft 45HP (ca. 21%, INCI name: Sodium Laureth-6 Carboxylate, Aqua; KAO); Protelan MST 35 (ca. 35%, INCI name: Sodium Myristoyl Sarconsinate, Sodium Methyl Cocoyl Taurate, Aqua; Zschimmer & Schwarz); Texapon K 14 S Special (ca. 70%, INCI name: Sodium Myreth Sulfate, Aqua; Cognis); Produkt W 37194 (ca. 20%, INCI name: Acrylamidopropyltrimonium Chloride/Acrylates Copolymer, Aqua; Stockhausen); Litchiderm LS 9704 (INCI name: Butylene Glycol; Lichti Chinensis Pericarp Extract; Laboratoires Serobiologiques).

The fatty base was melted together at 80° C. and dispersed with part of the water. The remaining components of the formulation were then successively incorporated with stirring. Water was then added to make up 100 wt % and the formulation was stirred without heating.

2) Developer Preparations EW

Table 2; Quantities in wt %

The following developer preparations were prepared with different polymeric thickeners.

| Raw material | E1 | E2 | V1 | V2 |
|---|---|---|---|---|
| Sodium hydroxide (45%) tech. | 0.73 | 0.73 | 0.73 | 0.73 |
| Dipicolinic acid | 0.10 | 0.10 | 0.10 | 0.10 |
| Disodium pyrophosphate | 0.03 | 0.03 | 0.03 | 0.03 |
| HEDP, aq., 60 wt % | 1.50 | 1.50 | 1.50 | 1.50 |
| Texapon NSO | 2.00 | 2.00 | 2.00 | 2.00 |
| Dow Corning DB 110A | 0.07 | 0.07 | 0.07 | 0.07 |
| Carbomer 954, aq., 4 wt % | 36.00 = 1.44 AS* | 45.00 = 1.80 AS* | — | — |
| Aculyn 33A | — | — | 5.14 = 1.44 AS* | 15.00 = 4.20 AS* |
| Hydrogen peroxide, aq., 50 wt % | 12.00 | 12.00 | 12.00 | 12.00 |
| Water, deionized | ad 100 | | | |

AS*: active substance

Raw materials: Texapon NSO (ca. 27%, INCI name: Sodium Laureth Sulfate; Cognis); Dow Corning DB 110 A (INCI name: Dimethicon; Dow Corning); Carbomer 954 (INCI name: Carbomer; Lubrizol); Aculyn 33A (ca. 28%; INCI name: Acrylates Copolymer, Aqua; Rohm & Haas).

3) Application Mixtures

Prior to use each of the developer solutions were added to the coloration cream FC in the weight ratio 1:1 and mixed together.

Mixtures were obtained with the following viscosities (Table 3):

| Colorant | Application Mixture | Thickener | Viscosity of the Mixture* [mPa s] |
|---|---|---|---|
| #1 | FC + E1 (inventive) | 0.72% AS** Carbomer 954 | 12400 |
| #2 | FC + E2 (inventive) | 0.90% AS** Carbomer 954 | 21100 |

-continued

| Colorant | Application Mixture | Thickener | Viscosity of the Mixture* [mPa s] |
|---|---|---|---|
| #3 | FC + V1 (non-inventive) | 0.72% AS** Aculyn 33 | 2000 |
| #4 | FC + V2 (non-inventive) | 2.10% AS** Aculyn 33 | 17100 |

*measured with a Brookfield-Viscosimeter DV-II+Pro with spindle #5 at 4 rpm at RT (22° C.) in 590 ml beakers, tall shape.
**active substance 4) Results In Table 3, it is clear that in spite of a significantly lower thickener content than preparation #4, the inventive colorant preparations #1 and #2 possess a suitable viscosity for use on human hair. If the quantity of thickener in the non-inventive colorant preparation #3 were reduced to the quantities of the preparations #1 and #2, the resulting viscosities of the mixtures would clearly be too low for the application.

The invention claimed is:

1. A cosmetic agent for changing a color of keratinic fibers, the cosmetic agent comprising:
    a preparation (M1) containing a color-changing component; and
    an oxidizing agent preparation (M2) containing in an aqueous, cosmetic carrier at least hydrogen peroxide as a chemical oxidizing agent and an anionic, polymeric thickener selected from crosslinked or uncrosslinked polyacrylic acid polymers
wherein the cosmetic agent has a viscosity of about 5 to about 100 Pa s, and wherein the cosmetic agent is prepared directly before use by blending the preparation (M1) with the oxidizing agent preparation (M2).

2. The cosmetic agent according to claim 1, wherein the preparation (M1) further comprises an oxidation dye precursor and/or a substantive dye as the color-changing component.

3. The cosmetic agent according to claim 1, wherein the preparation (M1) additionally comprises at least one alkalizer chosen from a group comprising ammonia, sodium hydroxide, sodium carbonate, potassium hydroxide, potassium carbonate, sodium hydrogen carbonate, ammonium carbonate, ammonium hydrogen carbonate, arginine, histidine, monoethanolamine, 2-amino-2-methylpropanol, an combinations thereof.

4. The cosmetic agent according to claim 1, wherein the anionic, polymeric thickener is selected from polyacrylic acids that have a molecular weight $M_w$ of at least about 500,000 g/mol.

5. The cosmetic agent according to claim 1, wherein the oxidizing agent preparation (M2) additionally comprises an anionic surfactant in a weight fraction of from about 0.05 to about 1.5 wt %, relative to a total weight of the oxidizing agent preparation (M2).

6. The cosmetic agent according to claim 1, wherein a pH of the cosmetic agent is from about 8.5 to about 11.5.

7. The cosmetic agent according to claim 6, wherein the pH of the cosmetic agent is from about 9.5 to about 11.5.

8. A multi-component packaging unit comprising:
    a first container (C1) containing a color-changing preparation (M1) comprising a color-changing component in a cosmetic carrier; and
    and a second container (C2) containing an oxidizing agent preparation (M2) comprising in an aqueous, cosmetic carrier at least hydrogen peroxide as a chemical oxidizing agent and additionally an anionic, polymeric thickener selected from crosslinked or uncrosslinked polyacrylic acid polymers,
wherein the first container (C1) and the second container (C2) are packaged separately from one another.

9. The multi-component packaging unit according to claim 8, wherein the color-changing preparation (M1) comprises an oxidation dye precursor as the color-changing component.

10. A method for changing a color of keratinic fibers using a multi-component packaging unit comprising:
    a first container (C1) containing a color-changing preparation (M1) comprising a color-changing component in a cosmetic carrier; and
    and a second container (C2) containing an oxidizing agent preparation (M2) comprising in an aqueous, cosmetic carrier at least hydrogen peroxide as a chemical oxidizing agent and additionally an anionic, polymeric thickener selected from crosslinked or uncrosslinked polyacrylic acid polymers,
wherein the first container (C1) and the second container (C2) are packaged separately from one another,
    the method comprising the steps of:
    combining the color-changing preparation (M1) with the oxidizing agent preparation (M2) in one of the first container (C1) or the second container (C2) to form a mixture;
    reclosing the one of the first container (C1) or the second container (C2);
    shaking the mixture to form a resulting, ready-for-use color-changing agent;
    applying the resulting, ready-for-use color-changing agent onto the keratinic fibers;
    leaving the resulting, ready-for-use color-changing agent on the keratinic fibers for a contact period of about 5 to about 60 minutes; and
    rinsing the resulting, ready-for-use color-changing agent out of the keratinic fibers.

11. The method according to claim 10, wherein the resulting, ready-for-use color-changing agent has a viscosity of about 5 to about 100 Pa s (Brookfield, 22° C., spindle #5, 4 rpm).

12. The method according to claim 11, wherein the resulting, ready-for-use color-changing agent has a viscosity of about 10 to about 30 Pa s.

13. The method according to claim 10, wherein applying comprises applying the resulting, ready-for-use color-changing agent onto human hair.

* * * * *